US008084218B2

(12) United States Patent
Ko et al.

(10) Patent No.: US 8,084,218 B2
(45) Date of Patent: Dec. 27, 2011

(54) METHOD FOR THE DIAGNOSIS OF CANCERS BY MEASURING THE CHANGES OF GLYCOSYLATION OF PROTEINS RELATED TO TUMORIGENESIS AND METASTASIS AND KIT FOR DIAGNOSIS OF CANCERS USING THE SAME

(75) Inventors: Jeong Heon Ko, Taejeon-si (KR); Soo Young Hwang, Seosan-si (KR); Hosung Sohn, Taejeon-si (KR); Sejeong Oh, Seoul (KR); Jeong Hwa Lee, Seoul (KR); Sang Chul Lee, Taejeon-si (KR); Jong-Shin Yoo, Taejeon-si (KR); Dae-Sil Lee, Taejeon-si (KR)

(73) Assignee: Korea Research Institute of Bioscience and Biotechnology, Taejeon-Si (KR)

( * ) Notice: Subject to any disclaimer, the term of this patent is extended or adjusted under 35 U.S.C. 154(b) by 100 days.

(21) Appl. No.: 12/615,180

(22) Filed: Nov. 9, 2009

(65) Prior Publication Data
US 2010/0099121 A1    Apr. 22, 2010

Related U.S. Application Data

(62) Division of application No. 10/499,920, filed as application No. PCT/KR02/02469 on Dec. 28, 2002, now Pat. No. 7,622,261.

(30) Foreign Application Priority Data

Dec. 29, 2001    (KR) .................. 10-2001-0088090

(51) Int. Cl.
G01N 33/53 (2006.01)
G01N 33/574 (2006.01)
G01N 33/00 (2006.01)

(52) U.S. Cl. .......... 435/7.1; 435/7.23; 435/7.5; 435/7.8; 435/7.9; 435/7.92

(58) Field of Classification Search .................. None
See application file for complete search history.

(56) References Cited

U.S. PATENT DOCUMENTS

| | | | |
|---|---|---|---|
| 4,994,374 | A | 2/1991 | Nishikawa et al. |
| 5,427,914 | A | 6/1995 | Dennis |
| 5,605,807 | A | 2/1997 | Dennis |
| 2003/0181369 | A1 | 9/2003 | Wildeman et al. |

FOREIGN PATENT DOCUMENTS

| | | |
|---|---|---|
| KR | 1999-0055111 | 7/1999 |
| KR | 1999-0069637 | 9/1999 |

OTHER PUBLICATIONS

Boyd (The Basic Science of Oncology, 1992, McGraw-Hill, Inc., p. 379).*
Busken et al., Digestive Disease Week Abstracts and Itinerary Planner, Abstract No. 850, 2003.
Carter et al., Chemotherapy of Cancer; Second Edition; John Wiley & Sons: New York, Appendix C, 1981.
Cummings and Kornfeld, "Characterization of the structural determinants required for the high affinity interaction of asparagine-linked oligosaccharides with immobilized Phaseolus vulgaris leukoagglutinating and erythroagglutinating lectins," *J. Biol. Chem.*, vol. 257, pp. 11230-11234, 1982.
Dermer, "Another Anniversary for the War on Cancer," *Bio/Technology*, vol. 12, p. 320, 1994.
Drexler et al., "Recent results on the biology of Hodgkin and Reed-Sternberg cells. II. Continuous cell lines," *Leukemia and Lymphoma*, vol. 9, pp. 1-25, 1993.
Ekuni et al., "A Glycomic Approach to Hepatic Tumors in N-Acetylglucosaminyltransferase III (GnT-III) Transgenic Mice Induced by Diethylynitorsamine (DEN): Identification of Haptoglogin as a Target Molecule of GnT-III," *Free Rad. Res.*, vol. 36, pp. 827-833, 2002.
Embleton et al., "Monoclonal Antibodies to Osteogenic Sarcoma Antigens," *Immunol Ser.*, vol. 23, pp. 181-207, 1984.
Freshney, Culture of Animal Cells, A Manual of Basic Technique, Alan R. Liss, Inc., New York, pp. 3-4, 1983.
Hakomori, "Glycosylation defining cancer malignancy: New wine in an old bottle," *Proc. Natl. Acad. Sci. USA*, vol. 99, pp. 10231-10233, 2002.
Harper et al., "Unit 10.4, Two-Dimensional Gel Electrophoresis," Current Protocols in Protein Science, p. 10.4.1-36, 1998.
Holmes, "PSMA specific antibodies and their diagnostic and therapeutic use," *Exp. Opin. Invest. Drugs*, vol. 10, No. 3, pp. 511-519, 2001.
Hsu, in Tissue Culture Methods and Applications, Kruse and Patterson, Eds, Academic Press, NY, pp. 764-767, 1973.
Kim, et al., "Functional Proteomics Study Reveals that N-Acetylglucosaminyltransferase V Reinforces the Invasive/Metastatic Potential of Colon Cancer through Aberrant Glycosylation on Tissue Inhibitor of Metalloproteinase-1," *Mol. Cell. Proteomics*, vol. 7 pp. 1-14, 2008.
Krontiris and Capizzi, Internal Medicine, 4th Edition, Editor-in-chief Jay Stein, Elsevier Science, Chapters 71-72, pp. 699-729, 1994.
Kultima et al., "Normalization and expression changes in predefined sets of proteins using 2D gel electrophoresis: A proteomic study of L-DOPA induced dyskinesia in an animal model of Parkinson's disease using DIGE," *BMC Bioinformatics*, vol. 7, Article 475, 2006.
Paralkar et al., "Cloning and Characterization of a Novel Member of the Transforming Growth Factor-β/Bone Morphogenetic Protein Family," *Journal of Biological Chemistry*, vol. 273, No. 22, pp. 13760-13767, 1998.
Reddy et al., "Glycosylation of the overlapping sequons in yeast external invertase: effect of amino acid variation on the site selectivity in vivo and in vitro," *Glycobiology*, vol. 9, No. 6, pp. 547-555, 1999.

(Continued)

Primary Examiner — Peter J Reddig
(74) Attorney, Agent, or Firm — Klarquist Sparkman, LLP

(57) ABSTRACT

The present invention relates to a method for diagnosing cancers by measuring proteins associated with tumorigenesis and metastasis, and a diagnostic kit using the same, particularly relates to the method for diagnosing cancers by measuring the changes of glycosylation of proteins and the kit for diagnosis of cancers using the said method. The method and kit of the present invention can effectively be used for the sensitive diagnosis of cancers comprising colon cancer, stomach cancer, lung cancer and liver cancer.

11 Claims, 7 Drawing Sheets

OTHER PUBLICATIONS

Rudd and Dwek, "Rapid, sensitive sequencing of oligosaccharides from glycoproteins," *Current Opin. Biotechnol.*, vol. 8, pp. 488-497, 1997.

Sumi et al., "Serial lectin affinity chromatography demonstrates altered asparagine-linked sugar-chain structures of prostate-specific antigen in human prostate carcinoma," *J. Chromatography B*, vol. 727, pp. 9-14, 1999.

Taber's Cyclopedic Medical Dictionary, F.A. Davis Company, p. 274, 1989..

Tanaka et al., "Efficient generation of antibodies to oncoproteins by using synthetic peptide antigens," *Proc. Natl. Acad. Sci. USA*, vol. 82, pp. 3400-3404, 1985.

Varki et al., Essentials of Glycobiology (http://www.ncbi.nlm.nih.gov/books/bv.fcgi?rid=glyco.section.77), 1999.

Varki et al., Essentials of Glycobiology (http://www.ncbi.nlm.nih.gov/books/bv.fcgi?rid=glyco.section.470), 1999.

Zellner et al., "Disparity in expression of protein kinase C alpha in human glioma versus glioma-derived primary cell lines: therapeutic implications," *Clin. Can. Res.*, vol. 4, pp. 1797-1802, 1998.

Zips et al., "New anticancer agents: in vitro and in vivo evaluation," *In vivo*, vol. 19, pp. 1-8, 2005.

Merriam-Webster Online (http://www.merriam-webster.com/cg/bin/dictionary?book=Dictionary &va=extent), 2008.

\* cited by examiner

METHOD FOR THE DIAGNOSIS OF CANCERS BY MEASURING THE CHANGES OF GLYCOSYLATION OF PROTEINS RELATED TO TUMORIGENESIS AND METASTASIS AND KIT FOR DIAGNOSIS OF CANCERS USING THE SAME

CROSS REFERENCE TO RELATED APPLICATIONS

This is a divisional of U.S. patent application Ser. No. 10/499,920, filed Jun. 9, 2004, now U.S. Pat. No. 7,622,261, issued Nov. 24, 2009, which is the U.S. National Stage of International Application No. PCT/KR02/02469, filed Dec. 28, 2002, which was published in English under PCT Article 21(2), which in turn claims the benefit of Korean Application No. 10-2001-0088090, filed Dec. 29, 2001. Each of these applications is herein incorporated by reference.

FIELD OF THE INVENTION

The present invention relates to a method for diagnosing cancers by measuring proteins associated with tumorigenesis and metastasis and a diagnostic kit using the same, more particularly, relates to a method for diagnosing cancers by measuring the changes of glycosylation of proteins, especially, the changes of N-linked sugar chains of proteins associated with tumorigenesis and metastasis and a diagnostic kit using the same.

SEQUENCE LISTING

A computer-readable form of the sequence listing in the form of the file named Sequence_listing.txt, which is 3,316 bytes and was created on Oct. 31, 2008, is herein incorporated by reference.

BACKGROUND ART OF THE INVENTION

In order to analyze the functions of proteins, two-dimensional electrophoresis has long been used. But recently, proteomics, a post-genome functional analyzing method, took the place of it, which was led by the development of mass spectrometer like MALDI-TOF and the establishment of easy methods for determining N-terminal amino acid sequences. The proteomics, though, is limited in use for the research of cancer caused by the result of highly complicated signal transduction, because proteomics is selectively available for the analysis of functions at one point of time although the human body is in dynamic motion. In order to detect a cancer, it is more important to investigate the increased expression or post-translational modification that are the result of signal transduction than to observe the appearance of new spots by staining. The amounts of proteins that can be detected by two-dimensional electrophoresis are too small to analyze by simple staining. Observing glycosylation of proteins can help overcome the above problem and correct the analytical errors based on post-translational modification. When a patient group with cancer was compared with a control group, it was difficult to find out the difference of spots between the two groups by general electrophoresis, in the meantime, it was possible to draw a clear line between the two groups by analyzing the changes of glycosylation with lectin. It is now called glycomics, that is, an upgraded analytical method overcoming difficulties in proteomics analysis characterized by tracing the changes of glycosylation of proteins while post-translational modification is occurring.

From observing cellular biological changes during tumorigenesis and metastasis processes, it is concluded that various kinds of glycoproteins or glycolipids on the surface of cell membrane are induced to go through "aberrant glycosylation" by the specific signal from oncogene, resulting in the changes of sugar chain that consecutively causes the changes of intercellular adhesion and recognition, resulting in tumorigenesis and metastasis in the event (Hakomori and Kannagi, 1983, *J. Natl. Cancer Inst.*, 71:231-251; Feizi, 1985, *Nature*, 314:53-571). When external stimuli come in, signals are transmitted via oncogene ras, transcription factor ets-1 to stimulate the expression of N-acetylglucosaminyltransferase V (GnT-V). GnT-V is an enzyme catalyzing a reaction attaching N-acetylglucosamine onto the β1,6 site of the basic sugar chain of a glycoprotein and is known to be directly associated with cancer invasion and metastasis (Dennis, et al., 1987, *Science*, 236:582-585). As for glycoproteins, basic sugar chain is formed in endoplasmic reticulum (ER) after a protein is synthesized, which moves to the Golgi apparatus. Then, sugars are added thereto by various glycotransferases resulted from various vital phenomena of cells. Primary sugar chains are formed by catalyzing of six N-acetylglucosaminyltransferases (I-VI). GnT-V, which forms β1,6-N-acetylglucosamine sugar chain, has been believed to be deeply associated with tumorigenesis and metastasis. GnT-V is located in Golgi apparatus. This enzyme makes target proteins be secreted to or out of the cell surface by causing the changes of sugar chains. At this time, glycoproteins recognize surface proteins of target cells and then adhere thereto, causing a cancer.

Dennis et al. (*Science* 236(4801): 582-585, 1987) first reported that the β1,6 branches were remarkably represented as cancer tissues were growing or during metastasis. A cell surface protein gp130 is one of the major target proteins of GnT-V and shows highly metastasis activity when β1,6 N-acetylglucosamine is added. GnT-V knockout mice were established using embryonic stem cells in which GnT-V was deficient and to which polyomavirus middle T antigen (referred "PyMT" hereinafter) viral oncogene was introduced in order to induce a cancer. As a result, the growth of cancer and metastasis induced by PyMT were remarkably inhibited in GnT-V knockout mice comparing with another normal mice group in which only PyMT was over-expressed (Granovsky, et al., 2000, *Nature Med.*, 6:306-312), and the growth of β1,6 branch caused high metastasis especially in mice with breast cancer. Recent studies support that the GnT-V activity of 33 types of hepatocellular carcinoma (HCC) tissues is fifty times as high as it's activity to normal tissues and four times as high as that of cancer surrounding tissues (Yao, et al., 1998, *J Cancer Res. Clin. Oncol.*, 124:27-307). And high metastatic activity was also confirmed when large intestine cancer cell line WiDr in which GnT-V was over-expressed was injected into immunodeficient mice in order to induce large intestine cancer or when angiogenesis was investigated by CAM analysis using fertilized eggs (Miyoshi, et al., 2001, unpublished results). Thus, GnT-V is believed to be associated with metastasis and have high metastatic activity regardless of types of tissues. GnT-V enzyme was purified from human lung cancer cells and a mouse kidney, and cDNA cloning and analysis of genomic structure and promoter of the enzyme have been made (Gu, et al., 1993, *J. Biochem*, 113:614-619; Soreibah, et al., 1993, *J. Biol. Chem.*, 268:15381-15385; Kang, et al., 1996, *J. Biol. Chem.*, 271:26706-26712). The present inventors also reported in a recent study that transcription factor ets-1 was deeply associated with the expression of GnT-V (Ko, et al., 1999, *J. Biol. Chem.*, 274(33): 22941-22948). As for large intestine cancer, it now takes the 4th highest incidence in both men and women owing to the changes of dietary life into western and the development of the cancer increases continuously. However, there is no way to diagnose colon cancer accurately except large intestine endoscopy, so far.

Thus, the present inventors detected β1,6-N-acetylglucosamine in which sugars were attached by GnT-V in cancer-induced cells and found out a novel glycoprotein showing the changes of sugar chains by analyzing amino acid sequences with a mass spectrometer. And the present inventors completed this invention by developing a method for diagnosing cancers by measuring the changes of sugar chains of the above protein in test samples and a diagnostic kit for cancers using the same.

DETAILED DESCRIPTION OF THE INVENTION

It is an object of the present invention to provide a method for diagnosing cancers by measuring the changes of sugar chains of proteins related to tumorigenesis and metastasis and a diagnostic kit using the same.

To achieve the above object, the present invention provides a method for diagnosing cancers by measuring the changes of sugar chains of proteins related to tumorigenesis and metastasis.

The present invention also provides a diagnostic kit for cancers using the above method.

Further features of the present invention will appear hereinafter.

To achieve the above object, the present invention provides a method for diagnosing cancers by measuring the changes of sugar chains of proteins related to tumorigenesis and metastasis.

Cancers stated above can be selected from a group consisting of colon cancer, gastric cancer, lung cancer, liver cancer, uterine cancer, breast cancer and pancreas cancer, but are not limited thereto.

The present invention provides a method for measuring the changes of sugar chain branches of proteins in cancer cells and metastatic cells representing the changes of β1,6 N-acetylglucosamine, that is the changes of N-linked sugar chains, by comparing them with those in normal cells. GnT-V forming sugar chains of β1,6 N-acetylglucosamine is associated with tumorigenesis and metastasis regardless of types of tissues, and the sugar chains of β1,6-N-acetylglucosamine can be detected with lectin phytohaemagglutinin-L4 (referred "L4-PHA" hereinafter).

Metastasis is caused by intercellular recognition and adhesion. Glycoproteins associated with intercellular recognition and adhesion, are on the cell surface or secreted therefrom. Thus, cancers can be diagnosed by detecting primary markers from body fluids like blood or urine. In the preferred embodiments of the present invention, a colon cancer cell line WiDr, in which GnT-V expression was comparatively low, was used in order to identify specific markers of large intestine cancer, and glycomics was performed using GnT-V/WiDr, a cell line over-expressing GnT-V, as a model system of colon cancer. In this invention, metastatic cancer cell culture solution was analyzed by 2-dimensional electrophoresis. As a result, 2 sheets of gel were obtained. One sheet of gel was stained with Coomassie brilliant blue and the other sheet was treated with lectin blotting. Finally, proteins in which sugar chains were changed in cancer cells and metastatic cells rather than in normal cells were separated (see FIG. 5 and FIG. 6). Some regions having strong dark spots were detected in cancer cells by lectin blot recognizing β1,6 N-acetylglucosamine branch. The proteins corresponding to the spots were confirmed to be associated with tumorigenesis and metastasis and show the changes of sugar chains.

The present inventors cut the spots off, and then cleaved proteins again. Amino acid sequence of the peptide was determined using Electrospray Ionization (ESI)/Quadruple Time of Flight (Q-TOF) mass spectrometer, resulting in the confirmation of peptide sequences represented by SEQ. ID. Nos 1-15. The peptide sequences were identified with precise names by comparing that with already established protein database and further analyzed each sequence, molecular weight and isoelectric point (see Table 1).

The above protein was confirmed based on the fact that N-linked sugar chain is located on the Asn in the sequence of Asn-Xaa-Thr/Ser (Varki, et al., 1999, *Essentials of glycobiology*, Cold Spring Harbor Laboratory, New York, USA, pp 85-100).

The peptide sequences analyzed above, which are represented by SEQ. ID. No 1 and No 2, are the parts of PDF (prostate-derived factor). In the meantime, PDF is known as one of BMPs (Bone morphogenetic proteins) that is a member of TGF-β (transforming growth factor beta) family and is associated with bone development and regeneration by inducing cartilage formation (Paralkar, V. M. et al., 1998, *J Biol. Chem*, 273:13760-13767). And the peptide has 2 well-reserved N-linked sugar chain sites. The above proteins have been found by many research groups in the name of PDF, MIC-1 (macrophage inhibitory cytokine-1), PLAB (placental bone morphogenic protein), GDF-15 (growth/differentiation factor 15), etc.

The peptide sequences analyzed above, which are represented by SEQ. ID. No 3, No 4 and No 5, are known as T cell cyclophilin and also called peptidyl-prolyl cis-trans isomerase. The reserved N-linked sugar chain can be found on 3 sites on the sequence that is also well known as a constituent for anti-oxidant system.

The peptide sequences analyzed above, which are represented by SEQ. ID. Nos 6-11, were confirmed to be a new protein by comparing that up with the entire established database. The protein has Asn-Xaa-Ser sequence in its 4th peptide, suggesting it probably contains N-linked sugar chain.

The peptide sequences analyzed above, which are represented by SEQ. ID. No 12 and No 13, are known in many names of galectin binding protein, L3 antigen, Mac-2-binding protein, serum protein 90K, tumor associated antigen 90K, etc, and are detected from the blood of cancer or AIDS patients. The result of Northern blot was that the protein was expressed much in primary cancer tissues and tumor-associated cell lines, though the expression varied with disease types. The protein was proved to have 7 reserved N-linked sugar chain sites (Ullich, A. et al., 1994, *J Biol. Chem.,* 269: 18401-18407).

The peptide sequences analyzed above, which are represented by SEQ. ID. No 14 and No 15, are known as TIMP-1 (tissue inhibitor of matrix metalloproteinase-1) and 4 TIMPs (1-4) have been found so far. As a low molecular protein, the molecular weights of the proteins are 22K-30K and the proteins have 40-50% homology. TIMP-1 takes the form of train by glycosylation, because of which the molecular weight of TIMP-1 seems to be high (see FIG. 7). And N-terminal is attached to MMPs, resulting in the inhibition of the activity of matrix metalloproteinase. This protein has N-linked sugar chains on two sites (Gomls-Reuth, F. et al., 1997, *Nature*, 389:77-81).

Even though two of the above five proteins, galectin binding protein (tumor associated antigen 90K) and TIMP-1, have been known to be directly related to tumorigenesis and metastasis, clear reports on the changes of sugar chain branches of β1,6 N-acetylglucosamine induced by cancer and the above two proteins have not been presented yet.

The proteins detected out above that reflect the changes of sugar chains in connection with tumorigenesis and metastasis are glycoproteins, and they are on the surface of cells or secreted therefrom, so that cancer can be diagnosed by measuring the expression and the changes of N-linked sugar chains of the proteins in body fluids like blood or urine.

A method for diagnosing cancers using the proteins related to tumorigenesis and metastasis comprises following two steps: Taking samples from patients (Step 1); and Measuring the changes of N-linked sugar chains and the expression of proteins related to tumorigenesis and metastasis with the above samples (Step 2).

The sample of the above Step 1 can be taken from blood or urine, and preferably prepared by the general separation method of serum.

As for the measuring method of the above Step 2, every analyzing methods based on the principle of antigen-antibody reaction can be used. Especially, ELISA (enzyme-linked immunosorbant assay) and immunoblot, the most common methods for analyzing antigen-antibody reaction, are preferably used.

The present inventors provide a method for measuring the changes of N-linked sugar chains and the expression of proteins related to tumorigenesis and metastasis after producing antibodies to the proteins in order to diagnose cancers.

A method for measuring the changes of N-linked sugar chains and the expression of the proteins by ELISA comprises the following steps:

1) Adhering antibody against the protein related to tumorigenesis and metastasis to matrix;
2) Adding serum of a sample to the above matrix to induce reaction, and then washing thereof;
3) Adding marked the same antibody or marked L4-PHA for further reaction;
4) After washing the above matrix, adding the secondary antibody conjugated with coloring enzyme or fluorescent substance thereto for further reaction; and
5) After coloring thereof using coloring substrate solution, measuring optical density with ELISA reader.

The matrix of the Step 1 can be selected from a group consisting of nitrocellulose membrane, 96 well plate synthesized with polyvinyl resin, 96 well plate synthesized with polystyrene and slide glass, and 96 well plate was chosen for this invention.

For a mark of the above Step 3, a chemical compound (or its derivatives) like biotin can be used. The expression of proteins related to tumorigenesis and metastasis can be analyzed using biotin-labeled the same antibody and the changes of β1,6 N-acetylglucosamine sugar chain branches, the changes of N-linked sugar chains, can be measured using biotin-labeled L4-PHA.

Peroxidase or alkaline phosphatase can be used as a coloring enzyme conjugated with antibody of the Step 4, and FITC or RITC can be used as a fluorescent substance. Particularly, peroxydase conjugated antibody was used in this invention.

ABTS [2,2'-Azino-bis(3-ethylbenzothiazoline-6-sulfonic acid)], OPD (o-Phenylenediamine) and TMB (Tetramethyl Benzidine) can be used as a coloring substrate solution of the Step 5, and particularly, OPD that was colored by peroxidase was used in this invention.

The method for diagnosing cancers of the present invention is available for mass-analysis of samples using biological microchip and automatic microarray system.

The present invention also provides a kit for diagnosing cancers by measuring the changes of sugar chains and the expression of proteins associated with tumorigenesis and metastasis.

Cancers mentioned above include large intestine cancer, stomach cancer, lung cancer, liver cancer, uterine cancer, breast cancer and pancreas cancer, but are not limited thereto, that is, any kind of cancer can be a target of this invention.

The protein associated with tumorigenesis and metastasis is selected from a group consisting of PDF, peptidyl-prolyl cis-trans isomerase, galectin binding protein, L3 antigen, Mac-2-binding protein, serum protein 90K, tumor associated antigen 90K, TIMP-1 and proteins containing peptide sequences represented by SEQ. ID. Nos 6-11.

The diagnostic kit of the present invention is available for qualitative analysis or quantitative analysis of the expression of the above proteins and for measuring the changes of N-linked sugar chain, exactly the changes of β1,6-N-acetylglucosamine sugar chain branches, for which ELISA can be used. For instance, the diagnostic kit can be provided for the ELISA using 96 well microtiter plate coated with antibody against the above proteins.

The diagnostic kit of the present invention can include antibody against the above proteins, matrix, buffer solution, coloring enzyme or fluorescent substance-labeled secondary antibody, coloring substrate, and especially, L4-PHA to measure the changes of β1,6-N-acetylglucosamine sugar chain branches.

As for the matrix, nitrocellulose membrane, 96 well plate synthesized with polyvinyl resin, 96 well plate synthesized with polystyrene resin, and slide glass can be used. As for the coloring enzyme, peroxidase and alkaline phosphatase can be used. As for the fluorescent substance, FITC and RITC can be used and as for the coloring substrate solution, ABTS (2,2'-Azino-bis(3-ethylbenzothiazoline-6-sulfonic acid)), OPD (o-Phenylenediamine), or TMB (Tetramethyl Benzidine) can be used.

In order to diagnose cancers with the diagnostic kit of the present invention, automatic analyzing method using biological microchip can be used. For example, the diagnostic kit can be composed to prepare a protein chip by fixing the proteins in which sugar chains are changed by being associated with tumorigenesis and metastasis onto the surface of glass slide and to measure the changes of those sugar chains of the proteins simultaneously. This diagnostic kit also includes the proteins, buffer solution and L4-PHA, etc.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Two-Dimensional Electrophoresis and Lectin Blotting of Cell Lines

The present inventors performed proteomics with GnT-V/WiDr cell line, considering that cell line as a model system of large intestine cancer. Particularly, cultured cells first, and then searched out a specific protein group evoking aggravation of cancer by being associated with the enzyme among intracellular and extracellular secreted proteins. Cultured Mock/WiDr, a control group cell line, ets-1/WiDr, a cell line over-expressing ets-1, and GnT-V/WiDr, a cell line over-expressing GnT-V, in RPMI medium (Gibco BRL) supplemented with 10% FCS. For the preparation of an over-expressing cell line, introduced eukaryotic over-expression plasmid (Ko, et al., 1999, J. Biol. Chem., 274(33): 22941-22948), transcription factor ets-1 and glycotransferase GnT-V into the large intestine cancer cell line WiDr (provided by American Type Tissue Culture; ATCC, USA). Treated the cells with G418 (350 μg/ml) to correspond to neomycin resistant gene. As colonies were formed, detected ets-1 with Western blot using antibody and GnT-V with Northern blot using cDNA. 2-3 days later, when cells covered 90% of the bottom of culture plate (confluent) in a $CO_2$ incubator, the cells were washed with PBS (phosphate buffered saline) more than twice to remove remaining serum. Collected the cells with a scraper and washed with PBS. Suspended the cells in 1 Ml of PBS and then sonicated thereof with a ultrasonicator (three times, 1 minute each time). Added acetone containing TCA (trichloroacetic acid) to the above crushed cells (final conc. 10%) to precipitate proteins only. Washed thereof with acetone more than three times to remove remaining TCA and then dried. Dissolved thereof by adding gel loading buffer solution (8 M Urea, 2% Triton X-100, 20 mM DTT, 0.5% carrier ampholyte, Bromophenol Blue dye) and performed 1-dimensional electrophoresis (18 cm drystrip pH 3-10) using Multiphor-II (Pharmarcia).

After equilibrating the obtained 1-dimensional electrophoresis gel with equilibrium buffer solution containing SDS and 2-mercaptoethanol, performed 2-dimensional electrophoresis on 12% polyacrylamide using Protean II (Bio-Rad). Obtained 2 sheets of gel: One was stained with Coomassie brilliant blue using biosafe staining solution (Bio-Rad) and the other was transferred to PVDF (polyvinylidene difluoride) membrane using semi-dry transfer (Bio-Rad). Adhered biotin-labeled L-PHA recognizing β1,6 N-acetylglucosamine branch to glycoprotein having the branch, and then attached HRP-labeled streptoavidin thereto. Exposed thereof to film by ECL fluorescent reaction.

Figure 1:
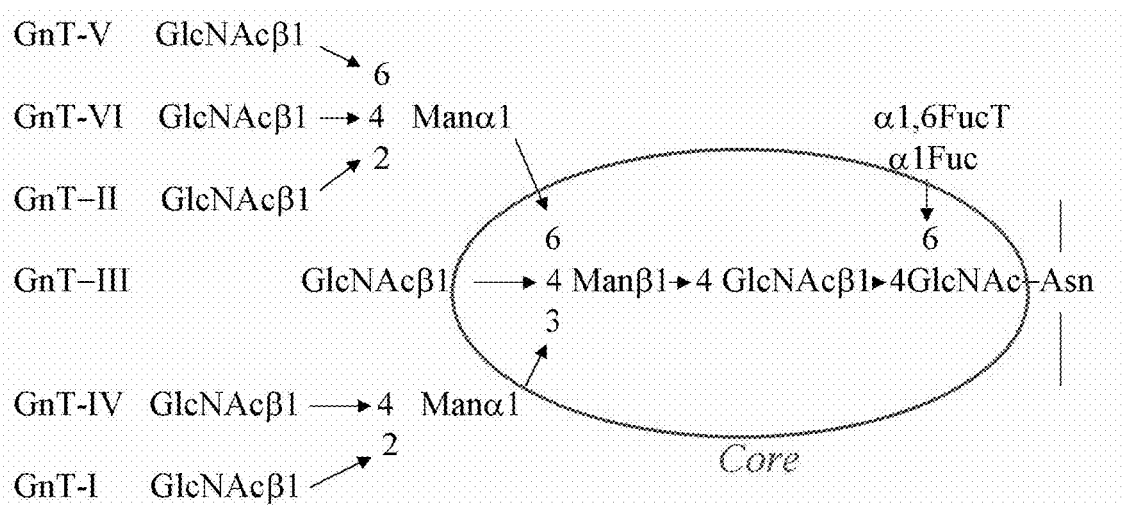
FIG. 1 is a diagram showing sugar chains obtained by the action of 6 glycotransferases related to N-linked sugar chain.
Figure 2:
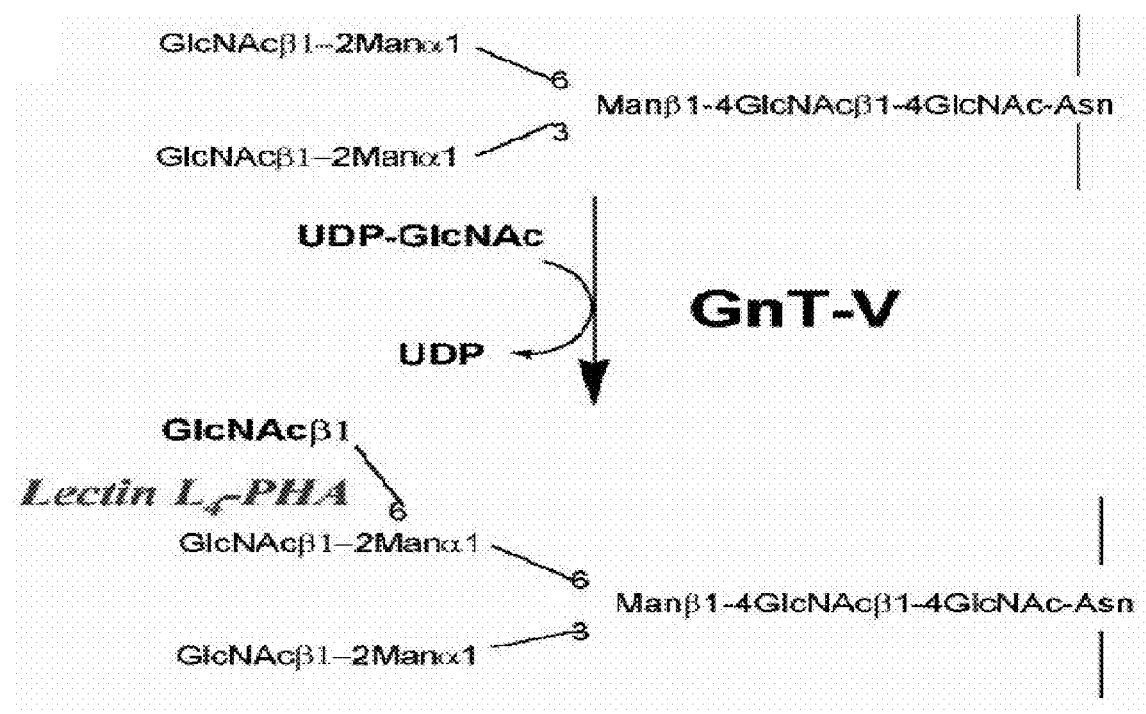
FIG. 2 is a set of diagrams showing the adding process of β1,6 N-acetylglucosamine (GlcNAcβ1) to sugar chain by glycotransferase GnT-V.
Figure 3:
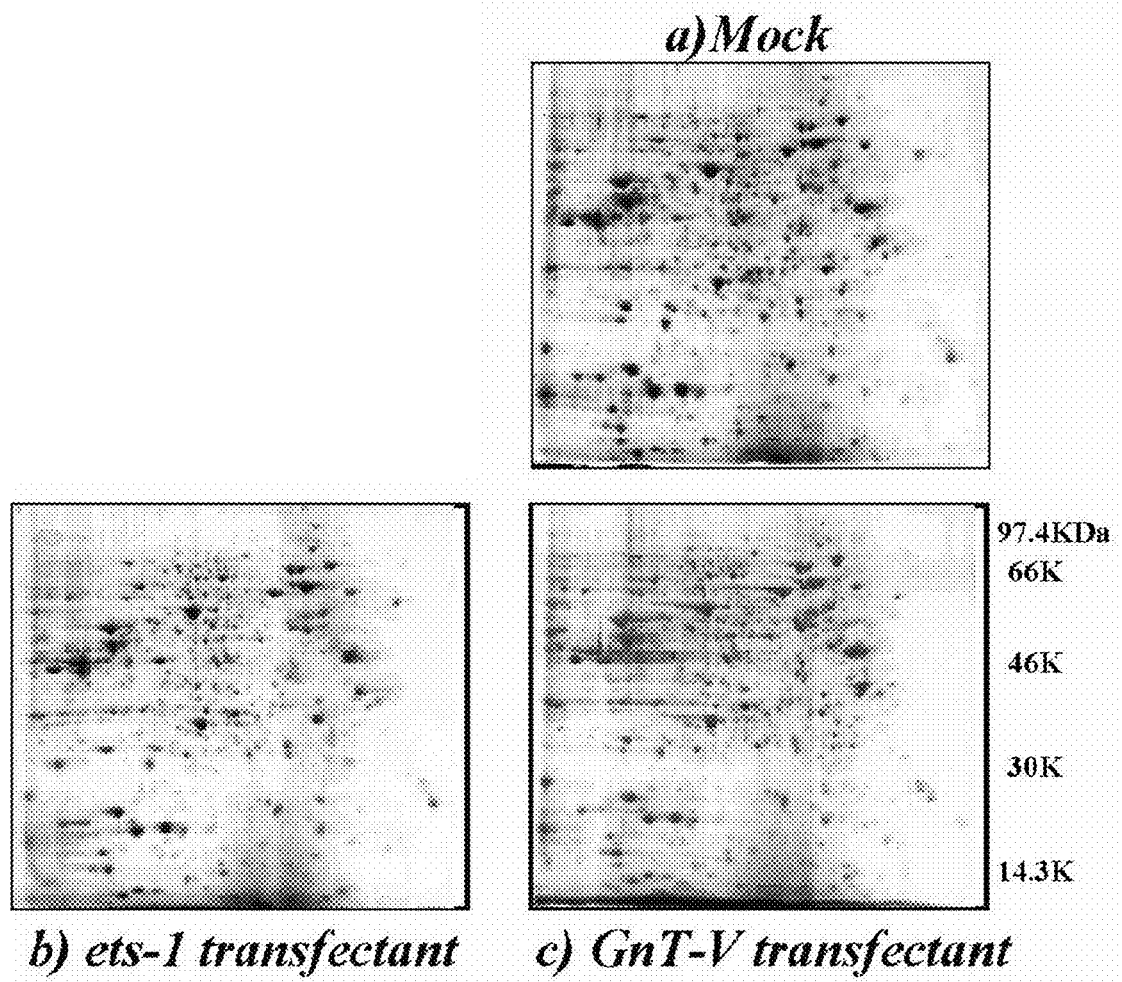
FIG. 3 is a set of photographs showing the results of staining gels obtained by 2-dimensional electrophoresis of three cell lines (Mock/WiDr, ets-1/WiDr, GnT-V/WiDr) with Coomassie brilliant blue.
Figure 4:
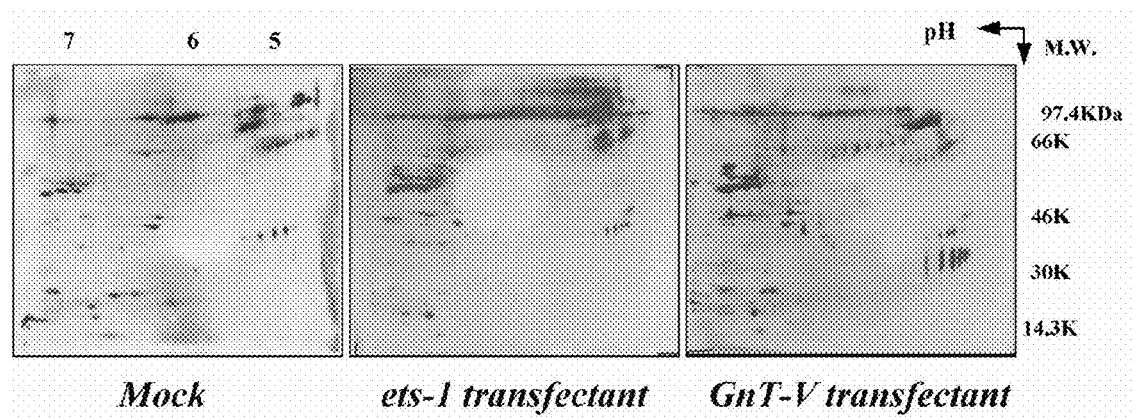
FIG. 4 is a set of photographs showing the results of lectin blotting with gels obtained by 2-dimensional electrophoresis of three cell lines.

In order to compare with a control group (Mock/WiDr), carried out the experiments with the same condition, that is, performed 1-dimensinal electrophoresis (separation of isoelectric point) first and then stained with Coomassie brilliant blue (FIG. 3), transferred the proteins of gel to PVDF membrane, followed by performing lectin blotting using GnT-V-specific L4-PHA (FIG. 4). Performed 2-dimensional electrophoresis more than three times and analyzed the changes of the expression of intracellular protein using computer software (PDQUEST, Bio-Rad). As a result, no protein that showed more than 4-times difference in the expression profile of protein was detected and no significant change was seen in lectin blot (FIG. 4), either.

Example 2

Two-Dimensional Electrophoresis and Lectin Blotting of Serum-Free Media

The present inventors cultured cell lines in serum-free media, through which investigated the changes of sugar chains. Particularly, cultured Mock/WiDr cell line, ets-1/WiDr cell line and GnT-V/WiDr cell line in RPMI (Gibco BRL) media containing 10% FCS. 2-3 days later, when cells covered around 80% of the bottom of culture plate in a $CO_2$ incubator washed with PBS more than twice to remove remaining serum. Then, put RPMI medium without serum, further cultured for 48 hours, and obtained culture solution. After concentrating the medium, added acetone (final conc. 10%) containing TCA (trichloro acetic acid), resulting in the precipitation of proteins. Washed thereof with acetone more than 3 times to remove remaining TCA, and then dried. Dissolved thereof by adding gel loading buffer solution (8 M Urea, 2% Triton X-100, 20 mM DTT, 0.5% carrier ampholyte, Bromophenol Blue dye) thereto. Performed 1-dimensional electrophoresis and 2-dimensional electrophoresis with the same method as the above Example 1.

Figure 5:
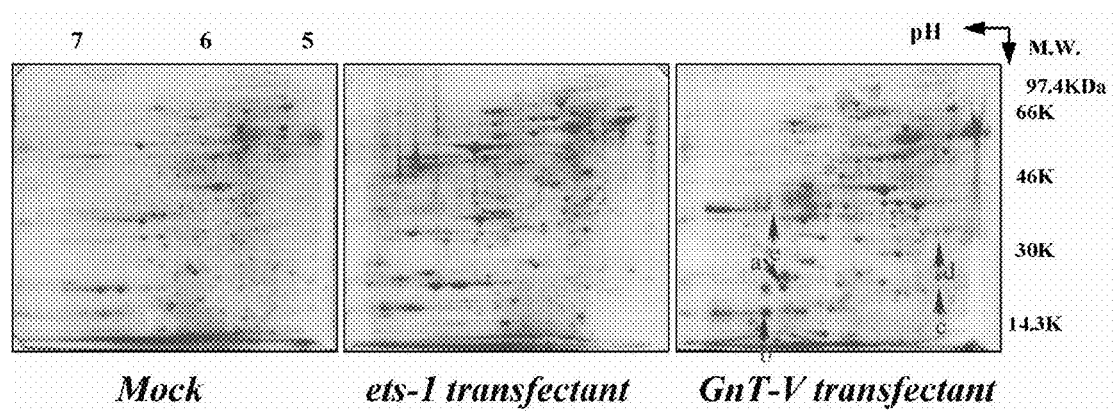
FIG. 5 is a set of photographs showing the results of staining serum-free media derived from three cell lines with Coomassie brilliant blue after 2-dimensional electrophoresis.
Figure 6:
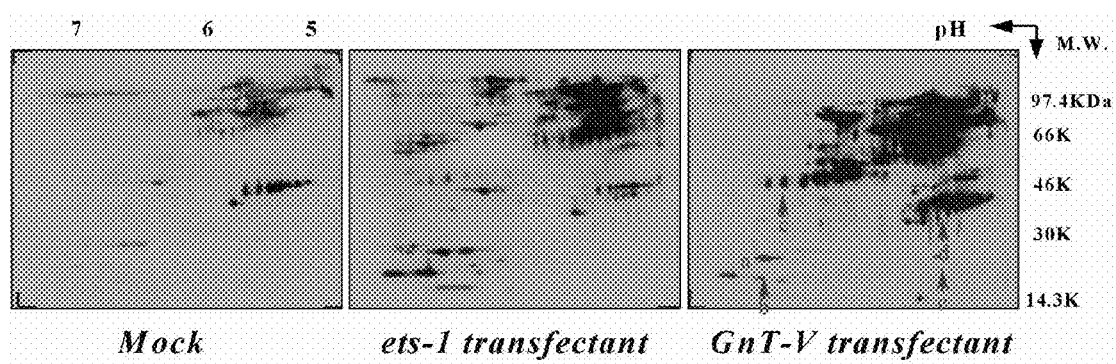
FIG. 6 is a set of photographs showing the results of lectin blotting on serum-free media derived from three cell lines with L4-PHA after 2-dimensional electrophoresis.

After completing 2-dimensional electrophoresis, small amounts of FCS were detected and wide changes of PIM (post translational modification) were expected, so that the expression could hardly be compared with limited software. In the mean time, it was confirmed from the result of L-PHA lectin blot that darker spots were detected in ets-1 over-expressing cell line, comparing with the control group, and the darkest spots were observed in GnT-V over-expressing cell line (FIG. 5 and FIG. 6). Cut 12 spots off among all the above spots and identified 5 spots of them.

Example 3

Sequence Analysis of Proteins with an ESI/Q-TOF Mass Spectrometer

In order to identify proteins located in the above 5 spots, the present inventors stained PVDF membrane (lectin blot) that was already exposed to X-ray film with Coomassie brilliant blue and then adhered thereof onto exposed film again to confirm the exact locations of spots, followed by cutting spots off corresponding to those of a gel stained with Coomassie brilliant blue. After destaining thereof using 30% methanol and 100% acetonitrile, added 10 U of trypsin (Promega) and then cut peptides at 37° C. for overnight. Extracted the peptides using acetonitrile, freeze-dried thereof with a centrifugal freezing drier, and then determined amino acid sequences using ESI/Q-TOF (Electrospray Ionization/Quadruple Time of Flight) mass spectrometer. Each peptide could be separated by ESI and sequence analysis could be possible by tandem mass.

As a result, sequences of peptide fragments represented by SEQ. ID. Nos 1-15 were determined by ESI/Q-TOF and identified after being compared with protein database. Each sequence, molecular weight (MW) and isoelectric point (pI) were presented below (Table 1).

TABLE 1

| No | Peptide fragment | Name | Function | M.W | pI | N-linked glycosylation |
|---|---|---|---|---|---|---|
| a | SEQ. ID. No 1<br>SEQ. ID. No 2 | GDF-15 | PLAB/TFG-β family | 34168.6 | 9.79 | Y |
| b | SEQ. ID. No 3<br>SEQ. ID. No 4<br>SEQ. ID. No 5 | Cyclophilin | Peptidyl-prolyl cis-trans isomerase A | 18012.7 | 7.86 | Y |
| c | SEQ. ID. No 6<br>SEQ. ID. No 7<br>SEQ. ID. No 8<br>SEQ. ID. No 9<br>SEQ. ID. No 10<br>SEQ. ID. No 11 | Not identified | Not identified | About 20K | About 5.5 | Y |
| d | SEQ. ID. No 12<br>SEQ. ID. No 13 | Galectin 3 binding protein | Galectin binding serum protein | 65331.6 | 5.13 | Y |
| e | SEQ. ID. No 14<br>SEQ. ID. No 15 | TIMP-1 | Tissue inhibitor of matrix metalloproteinase | 23171.1 | 8.46 | Y |

Their characteristics are explained below. The above proteins were confirmed based on the fact that N-linked sugar chain is located on the Asn in the sequence of Asn-Xaa-Thr/Ser (Varki, et al., 1999, *Essentials of glycobiology*, Cold Spring Harbor Laboratory, New York, USA, pp 85-100).

A of the above Table 1 containing peptide sequences represented by SEQ. ID. No 1 and No 2, that is PDF (prostate-derived factor), is one of BMP proteins (Bone morphogenetic proteins) of TGF (transforming growth factor)-β family and has two preserved N-linked sugar chain sites. This protein has been searched in many names of not only PDF but also MIC-1 (macrophage inhibitory cytokine-1), PLAB (placental bone morphogenic protein), GDF-15, PTGFP, etc by many research groups.

B known as T cell cyclophilin containing peptide sequences represented by SEQ. ID. No 3, No 4 and No 5 is also called peptidyl-prolyl cis-trans isomerase. It has three preserved N-linked sugar chain sites.

C containing all the peptide fragments having amino acid sequences represented by SEQ. ID. Nos 6-11 is proved to be a new single protein by comparing it with the established databases. It is also believed to have N-linked sugar chain since it has the sequence of Asn-Xaa-Ser in its forth peptide.

D containing peptide sequences represented by SEQ. ID. No 12 and No 13 has been known in many names such as galectin binding protein, L3 antigen, Mac-2-binding protein, serum protein 90K, tumor associated antigen 90K, etc, and has seven preserved N-linked sugar chain sites.

Figure 7:
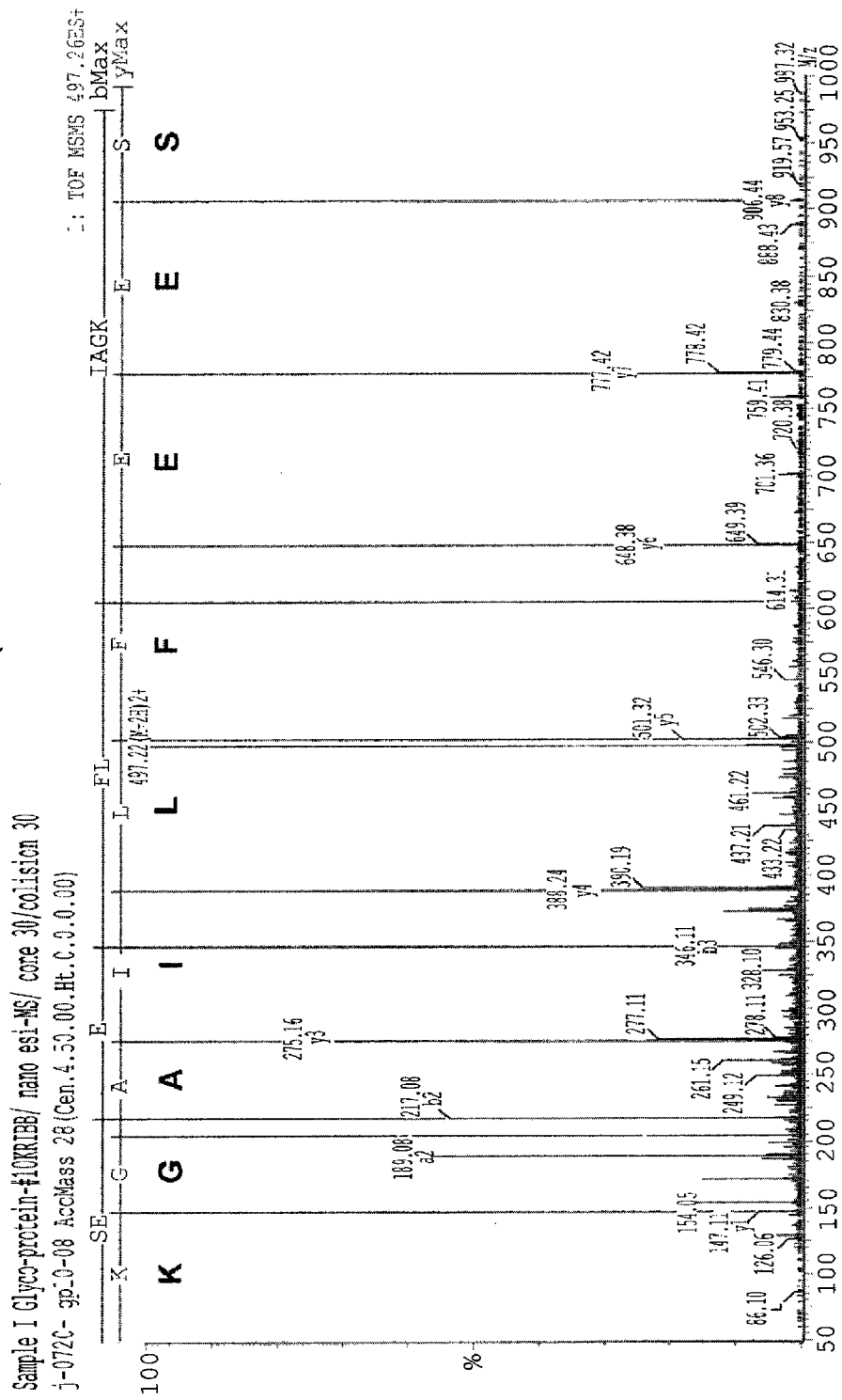
FIG. 7 is a graph showing the result of analysis of timp-1 amino acid sequence by ESI/Q-TOF (SEQ ID NO: 14).

E containing peptide sequences represented by SEQ. ID. No 14 and No 15 is known as TIMP-1 (tissue inhibitor of matrix metalloproteinase-1) and is an example of the above timp-1 identified by ESI/Q-TOF (FIG. 7). As shown in FIG. 7, TIMP-1 is shaped as a train formed by glycosylation, by which its molecular weight seems high. TIMP-1 also has two N-linked sugar chain sites.

Example 4

Measurement of the Changes of Sugar Chain Branches or the Expression of Proteins In order to diagnose cancers by measuring the changes of sugar chains or the expression of proteins identified above, the present inventors measured the changes of sugar chains and the expression of the proteins using ELISA.

First, obtained cDNA of target protein, which was then cloned into the eukaryotic gene expression vector. Cloned thereof into WiDr cell line. Purified the protein (1 mg each) from the above culture solution. Mixed thereof with adjuvant, which was injected hypodermically into rabbits, resulting in the preparation of polyclonal antibodies. Adhered the required amount of the antibody to two 96 well plates respectively. Precisely, coated protein A originated from bacteria to 96 well plate (Maxisorb, Nunc) by 1 μg per well under the condition of containing 100 μl of 0.1 M sodium carbornate (pH 9.6). Washed thereof with TBS-T (Tris-buffered saline-Tween, 0.2 M Tris-Cl, 0.4 M NaCl, 0.05% Tween-20) and adhered the above prepared antibody thereto. Washed with TBS-T again and then blocked parts that were not adhered, resulting in the preparation of a stable antibody system. Consecutive dilution was performed after adding blood or other test samples to the plate for the reproducibility and statistical handling, and then washed thereof with TBS-T three times. At that time, the target protein would be adhered to its specific antibody. The expression of the protein was confirmed by the same antibody labeled with biotin, and the changes of sugar chains of β1,6 N-acetylglucosamine were confirmed by lectin, in which biotin-labeled L-PHA was used. In order to prepare biotin-labeled antibody, dialyzed antibody (5-10 mg/Ml) in 250 Ml of SBRB (succinimidyl-biotin reaction buffer) at 23° C. for 6 hours. Adjusted the concentration of NHS-biotin (N-hydroxysuccinimidyl-biotin) or NHS-LC-biotin (long chain sulfosuccinimidyl 6-(biotinamido) hexanoate derivative biotin) to 2-4 mg/Ml in DMSO (dimethylsulfoxide) and mixed the antibody and the biotin solution in the ratio of 1:30 (Ab:biotin), followed by stirring at 37° C. Left thereof for 1 hour to bind biotin and antibody. Prepared biotin-labeled antibody after dialyzing thereof in BBS (Borate buffered saline). For the lectin, commercial biotin-labeled L-PHA was used. Detected biotin-labeled antibody and lectin by using commercial avidine-peroxidase kit. Precisely, added $H_2O_2$ and O-phenylamine, a substrate for peroxidase, and measured optical density at 490 nm. Measured the expression of protein and the changes of glycosylation of $\beta 1,6$ N-acetylglucosamine in the blood samples of patients with cancer and then compared them with those in normal control group.

As a result, the glycosylation extent of $\beta 1,6$ N-acetylglucosamine in the blood of cancer patients was confirmed to increase 10-20 times as much as that in normal blood.

INDUSTRIAL APPLICABILITY

As described hereinbefore, a method for diagnosing cancers by measuring the changes of sugar chains of proteins associated with tumorigenesis and metastasis, and diagnostic kit using the same of the present invention can be effectively used for diagnosing cancers including large intestine cancer.

We claim:

1. A method for diagnosing a colon cancer by measuring an extent of β1,6 N-acetylglucosamine glycosylation and an expression level of tissue inhibitor of matrix metalloproteinase-1 (TIMP-1) protein related to tumorigenesis and metastasis, comprising:
   - measuring an expression level of TIMP-1 protein in a colon, blood, or serum test sample isolated from a subject, wherein the expression level of TIMP-1 protein is measured using a labeled antibody against the TIMP-1 protein;
   - measuring an extent of β1,6 N-acetylglucosamine glycosylation of the TIMP-1 protein in the test sample, wherein the extent of β1,6 N-acetylglucosamine glycosylation of the TIMP-1 protein is measured using labeled L4-PHA; and
   - comparing the expression of the TIMP-1 protein and the extent of β1,6 N-acetylglucosamine glycosylation of the TIMP-1 protein between the test sample and a control sample, wherein an increase in the expression level of the TIMP-1 protein and the extent of β1,6 N-acetylglucosamine glycosylation of the TIMP-1 protein in the test sample relative to the control sample indicates presence of the colon cancer.

2. The method of claim 1, wherein the labeled antibody is a biotin-labeled antibody.

3. The method of claim 1, wherein the labeled L4-PHA is biotin-labeled L4-PHA.

4. The method of claim 2, further comprising:
   - adding a coloring enzyme- or fluorescent substance-conjugated avidin; and
   - measuring the optical density or detecting fluorescence, thereby measuring the expression level of the TIMP-1 protein in the test sample.

5. The method of claim 3, further comprising:
   - adding a coloring enzyme- or fluorescent substance-conjugated avidin; and
   - measuring the optical density or detecting fluorescence, thereby measuring the extent of β1,6 N-acetylglucosamine glycosylation of the TIMP-1 protein in the test sample.

6. The method of claim 4, wherein the coloring enzyme is selected from the group consisting of peroxidase and alkaline phosphatase.

7. The method of claim 5, wherein the coloring enzyme is selected from the group consisting of peroxidase and alkaline phosphatase.

8. The method of claim 4, wherein the fluorescent substance is selected from the group consisting of fluorescein isothiocyanate (FITC) and rhodamine-B-isothiocyanate (RITC).

9. The method of claim 5, wherein the fluorescent substance is selected from the group consisting of fluorescein isothiocyanate (FITC) and rhodamine-B-isothiocyanate (RITC).

10. A method for diagnosing colon cancer by measuring an extent of β1,6 N-acetylglucosamine glycosylation and an expression level of tissue inhibitor of matrix metalloproteinase-1 (TIMP-1) protein related to tumorigenesis and metastasis, comprising:
   - adhering antibodies against the TIMP-1 protein to two matrices, wherein one matrix is for analyzing expression of the TIMP-1 protein and the other is for analyzing extent of β1,6 N-acetylglucosamine glycosylation of the TIMP-1 protein;
   - adding a blood or serum test sample isolated from a subject to the two matrices to induce a first reaction;
   - adding biotin-labeled antibodies against the TIMP-1 protein to the one matrix for analyzing expression of the TIMP-1 protein and adding biotin-labeled L4-PHA to the other matrix for analyzing extent of β1,6 N-acetylglucosamine glycosylation of the TIMP-1 protein to induce a second reaction;

adding a coloring enzyme- or fluorescent substance-conjugated avidin to both matrices to induce a third reaction;

measuring the optical density or detecting fluorescence; and comparing the expression of the TIMP-1 protein and the extent of β1,6 N-acetylglucosamine glycosylation of the TIMP-1 protein between the test sample and a control sample, wherein an increase in the expression level of the TIMP-1 protein and the extent of β1,6 N-acetylglucosamine glycosylation of the TIMP-1 protein in the test sample relative to the control sample indicates presence of the colon cancer.

11. The method of claim 10, wherein the matrix is selected from the group consisting of a nitrocellulose membrane, a 96 well plate synthesized with polyvinyl resin, a 96 well plate synthesized with polystyrene resin, and slide glass.

* * * * *

SEQUENCE LISTING

```
<160> NUMBER OF SEQ ID NOS: 15

<210> SEQ ID NO 1
<211> LENGTH: 14
<212> TYPE: PRT
<213> ORGANISM: Homo sapiens

<400> SEQUENCE: 1

Gly Val Ser Ser Leu Gln Thr Tyr Asp Asp Leu Leu Ala Lys
1               5                   10

<210> SEQ ID NO 2
<211> LENGTH: 13
<212> TYPE: PRT
<213> ORGANISM: Homo sapiens

<400> SEQUENCE: 2

Glu Asp Leu Gly Trp Ala Asp Trp Val Leu Ser Pro Arg
1               5                   10

<210> SEQ ID NO 3
<211> LENGTH: 9
<212> TYPE: PRT
<213> ORGANISM: Homo sapiens

<400> SEQUENCE: 3

Val Ser Phe Glu Leu Phe Ala Asp Lys
1               5

<210> SEQ ID NO 4
<211> LENGTH: 9
<212> TYPE: PRT
<213> ORGANISM: Homo sapiens

<400> SEQUENCE: 4

Phe Glu Asp Glu Asn Phe Ile Leu Lys
1               5

<210> SEQ ID NO 5
<211> LENGTH: 19
<212> TYPE: PRT
<213> ORGANISM: Homo sapiens

<400> SEQUENCE: 5

Asn Val Asn Pro Thr Val Phe Phe Asp Leu Ala Val Asp Gly Glu Pro
1               5                   10                  15

Leu Gly Arg

<210> SEQ ID NO 6
```

```
<211> LENGTH: 8
<212> TYPE: PRT
<213> ORGANISM: Homo sapiens

<400> SEQUENCE: 6

Phe Thr Gly Gly His Glu Val Lys
1               5

<210> SEQ ID NO 7
<211> LENGTH: 12
<212> TYPE: PRT
<213> ORGANISM: Homo sapiens

<400> SEQUENCE: 7

Gly Leu Gly Ala Ser Asp Ser Thr Leu Thr Tyr Arg
1               5                   10

<210> SEQ ID NO 8
<211> LENGTH: 13
<212> TYPE: PRT
<213> ORGANISM: Homo sapiens

<400> SEQUENCE: 8

Asp Asn Asn Leu Gly Gln Ala Phe Gln Phe Glu Asp Arg
1               5                   10

<210> SEQ ID NO 9
<211> LENGTH: 11
<212> TYPE: PRT
<213> ORGANISM: Homo sapiens

<400> SEQUENCE: 9

Glu Phe Gly Leu Gly Ala Thr Ser Asp Ser Tyr
1               5                   10

<210> SEQ ID NO 10
<211> LENGTH: 10
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is any amino acid

<400> SEQUENCE: 10

Val Gly Asp Asn Xaa Leu Gly Ala Asn Ser
1               5                   10

<210> SEQ ID NO 11
<211> LENGTH: 6
<212> TYPE: PRT
<213> ORGANISM: Homo sapiens

<400> SEQUENCE: 11

Ser Gly Ala Tyr Thr Tyr
1               5

<210> SEQ ID NO 12
<211> LENGTH: 13
<212> TYPE: PRT
<213> ORGANISM: Homo sapiens

<400> SEQUENCE: 12

Gln Thr Pro Gln His Pro Ser Phe Leu Phe Gln Asp Lys
1               5                   10
```

```
<210> SEQ ID NO 13
<211> LENGTH: 20
<212> TYPE: PRT
<213> ORGANISM: Homo sapiens

<400> SEQUENCE: 13

Tyr Tyr Pro Tyr Gln Ser Phe Gln Thr Pro Gln His Pro Ser Phe Leu
1               5                   10                  15

Phe Gln Asp Lys
            20

<210> SEQ ID NO 14
<211> LENGTH: 9
<212> TYPE: PRT
<213> ORGANISM: Homo sapiens

<400> SEQUENCE: 14

Ser Glu Glu Phe Leu Ile Ala Gly Lys
1               5

<210> SEQ ID NO 15
<211> LENGTH: 6
<212> TYPE: PRT
<213> ORGANISM: Homo sapiens

<400> SEQUENCE: 15

Gln Ala Leu Gly Asp Ala
1               5
```